(12) United States Patent
Tivig et al.

(10) Patent No.: US 7,225,091 B2
(45) Date of Patent: May 29, 2007

(54) METHOD AND DEVICE FOR MONITORING A SYSTEM

(75) Inventors: Gerhard Tivig, Böblingen (DE);
Sebastian Hebler, Bad Lausick (DE);
Georg Eberhardt, Schelkingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/565,397

(22) PCT Filed: Jul. 13, 2004

(86) PCT No.: PCT/IB2004/051206

§ 371 (c)(1),
(2), (4) Date: Jan. 20, 2006

(87) PCT Pub. No.: WO2005/010756

PCT Pub. Date: Feb. 3, 2005

(65) Prior Publication Data

US 2006/0189851 A1 Aug. 24, 2006

(30) Foreign Application Priority Data

Jul. 25, 2003 (EP) .................................. 03102293

(51) Int. Cl.
*A61B 5/00* (2006.01)

(52) U.S. Cl. .................... 702/67; 600/300; 382/128; 345/156; 715/828; 715/961

(58) Field of Classification Search ............... 702/67, 702/19; 600/300, 481–484, 529, 301, 513; 345/168, 156; 382/128; 715/828, 961
See application file for complete search history.

(56) References Cited

U.S. PATENT DOCUMENTS

| 4,562,843 A | * | 1/1986 | Djordjevich et al. ......... 600/485 |
| 5,772,599 A | * | 6/1998 | Nevo et al. .................. 600/483 |
| 5,819,741 A |   | 10/1998 | Karlsson et al. ............. 128/710 |
| 6,174,283 B1 | * | 1/2001 | Nevo et al. .................. 600/301 |
| 6,224,549 B1 |   | 5/2001 | Drongelen ................... 600/300 |
| 6,383,136 B1 |   | 5/2002 | Jordan ........................ 600/300 |

FOREIGN PATENT DOCUMENTS

WO  WO 02/078540 A1  10/2002

\* cited by examiner

*Primary Examiner*—John Barlow
*Assistant Examiner*—Hien Vo
(74) *Attorney, Agent, or Firm*—Thomas M. Lundin

(57) ABSTRACT

The present invention relates to a method for monitoring a system in which a datum-line display (11) is generated on a viewing screen (4) for at least one parameter of the system, comprising a baseline (14) that represents a base value for the parameter concerned, a continuous curve (15) that represents a variation with time of the values of the parameter concerned and is normal with respect to the baseline (14), and a deviation bar (16) that represents the instantaneous deviation between the base value and current parameter value and is normalized with respect to the baseline (14).

15 Claims, 2 Drawing Sheets

METHOD AND DEVICE FOR MONITORING A SYSTEM

Figure 1:
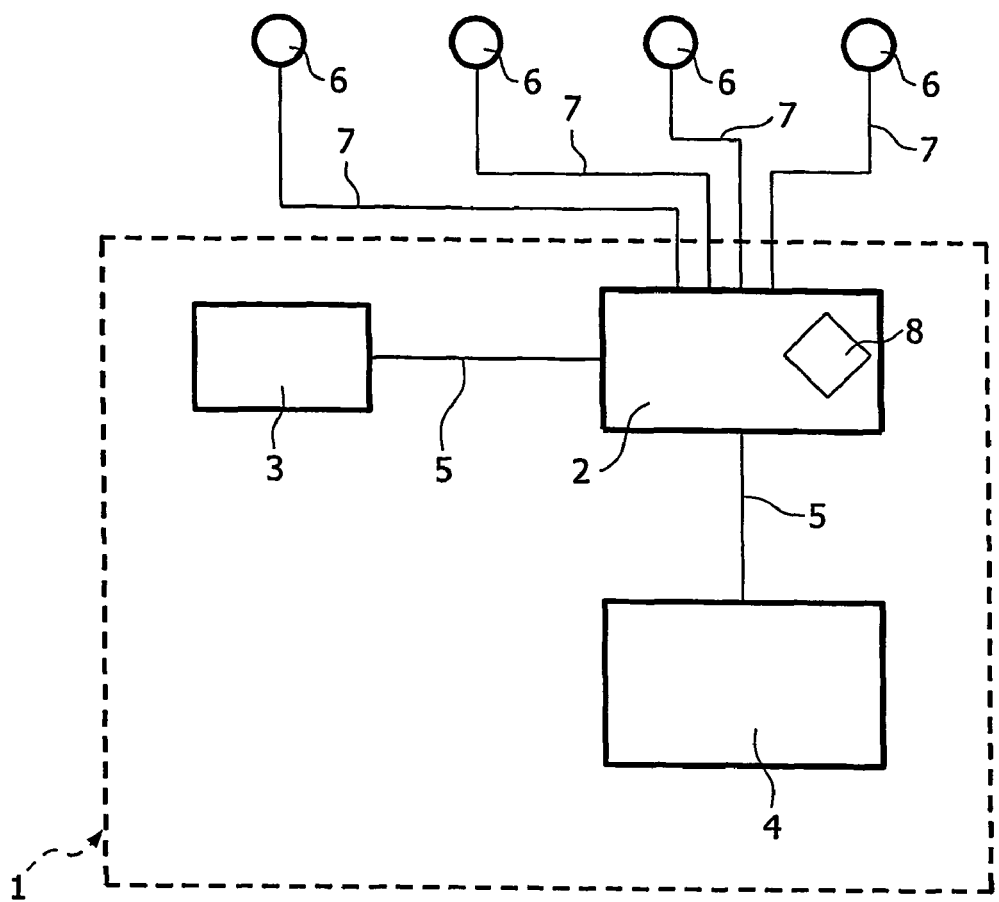

The present invention relates to a method and to a device for monitoring a system and, in particular, for displaying the status of the system.

In many fields, it is necessary to monitor and to analyze large amounts of data that are assigned to a certain system in order to be able to assess the current state of the system within a short time. For example, in the medical field, patients always form a system in which physiological parameters, such as, for example, pulse, blood pressure, respiratory rate, etc., have to be monitored if the patient is being operated on or is in an intensive care unit. In this connection, it is normal that 30 to 50 parameters have to be monitored simultaneously in the case of an individual patient. Likewise, within the framework of his work, a financial adviser must regularly monitor a multiplicity of parameters that may influence, for example, the share prices in order to be able to advise his clients appropriately. In this connection, the monitored system is the market and the associated parameters are, for example, closing price, yearly high, yearly low, dividends, previous-day price, price variation in the last quarter, etc. Furthermore, fairly large technical installations, such as, for example, a power station or an air traffic control center form a system whose correct functioning can be monitored on the basis of suitable parameters.

It has been found that the multiplicity of data monitored makes difficult a rapid and reliable diagnosis of the current system state, with the result that the wealth of the information items provided, for example in stress situations, already form a source of incorrect diagnoses. In particular, in clinical applications, the hospital staff have to filter out the information items particularly important for assessing the state of the patient from the large amount of data provided. In the case of complexly mutually interconnecting data, the risk of an incorrect diagnosis may increase under these circumstances if a decision essential for the life of the patient concerned has to be taken within a very short time. There is therefore the urgent need to process the parameters of the system to be monitored in such a way that it is more readily possible for the monitoring staff concerned to recognize the current system status and thus to simplify the taking of the correct decision in each case for the monitoring staff.

From U.S. Pat. No. 6,174,283, it is known to display a plurality of parameters in a parameter value display on a viewing screen in order to monitor a patient. In this case, the parameter value display contains a continuous curve for every associated parameter that represents the variation with time of the parameter concerned. In this connection, a suitable number of continuous curves are displayed above one another and expediently characterized by different colors in the parameter value display in accordance with the number of parameters provided. In addition to the continuous curves, the parameter value display contains, for every parameter displayed, a separate block in which a base value, an upper limit value and a lower limit value are displayed numerically for each case for the parameter concerned.

In the known methods, a deviation from the associated base value is determined for the parameter monitored in each case. In doing so, said deviation is correlated with the upper or with the lower limit value, respectively, of the parameter concerned. This generates deviation indicators that indicate how far the current parameter is removed from the base value. The deviations are in this case displayed on the viewing screen in the form of integers that are chosen, for example, from a range of 0 to 5. The greater the number is, the greater is also the deviation of the current parameter upward or downward from the base value.

In order to be able to display the deviation indicators on the viewing screen in a more readily recognizable way, a short-term display is provided in which the integral deviation indicators are displayed as a continuous curve. Furthermore, the short-term display contains a variation mean-value curve. Displayed alongside the continuous curve is a bar that additionally displays the value of the current deviation indicator.

In the known method, a long-term display is provided in addition that likewise displays a continuous curve and a variation mean-value curve of the deviation indicators, but for a longer period of time than in the case of the short-term display.

In the known method, a status indicator is determined from the deviation indicators that is displayed in the form of a field with a colored background on the viewing screen alongside the short-term display or alongside the long-term display. In this connection, a separate color is assigned to every numerical level of the deviation indicators in order thus to be able to visualize the state concerned better. If, for example, the respiratory rate of the patient deviates from the base value in the direction of the lower limit value, depending on the scale chosen for the time axis, this can be detected more or less well at the more recent end of the associated continuous curve in the parameter value display. On looking at the viewing screen, this segment of the continuous curve concerned may easily be lost and overlooked in the wealth of information items. With increasing deviation from the base value, the deviation indicator is increased in steps, which is clearly detectable from the short-term display, in particular from its bars. Furthermore, the color changes in the field of the associated status indicator. The user can, consequently, detect relatively easily that a certain parameter is relatively far away from the base value in magnitude. In addition, an additional direction display in the form of an arrow makes it possible for the user to detect whether the known deviation from the base value is taking place upward or downward. Alternatively, the user may also search the associated continuous curve in order to detect the direction of the deviation.

In the known method, the user has to bring together the information important to him at a plurality of points that are displayed in a distributed manner on the viewing screen. In order to link the related information items with one another, an increased concentration and possibly a relatively large amount of time is therefore necessary. In the clinical field, in particular, it may be necessary to take life-saving decisions for the patient within the shortest time, with the result that only a little time is available for bringing together the necessary information items.

The present invention is concerned with the problem of providing a better embodiment for a method and a device of the type mentioned at the outset, which embodiment facilitates, in particular, the monitoring of the system or of individual parameters of the system for the user concerned.

According to the invention, the subject matters of the independent claims solve this problem. The dependent claims relate to advantageous embodiments.

The invention is based on the general idea of creating, for at least one parameter of the system to be monitored, a datum-line display on a viewing screen that comprises a horizontal baseline representing the base value of the parameter, a continuous curve representing the variation with time of the parameter with a horizontal time axis and, in addition, a deviation bar representing the instantaneous deviation of the parameter from the base value. In addition, the continuous curve and the deviation bar are normalized with respect to the baseline. The datum-line display proposed according to the invention consequently comprises extremely few elements and their complete information can be discerned at a single glance. As a result of the normalization of the continuous curve and the deviation bar with respect to the baseline, the user can immediately detect visually whether the parameter concerned is deviating within its variation or is currently deviating to a small or considerable extent and, in particular, in which direction from the base value. The user does not consequently have to change back and forth between a plurality of displays for these basic information items, but can on the contrary, detect them at a single glance. In this connection, the invention takes account of the fact that deviations with respect to a horizontally displayed baseline can particularly easily be detected intuitively by the user.

According to a particularly advantageous embodiment, the datum-line display may have a trend arrow generated by determining the trend or instantaneous slope of the continuous curve in the current parameter value and that creates the trend arrow representing the instantaneous slope or trend and is displayed on the viewing screen. The trend arrow provides for the user an instrument that enables him to detect at a single glance the direction in which the parameter concerned will evolve in the immediate future with increased probability. This additional information may be particularly important in the individual case. The trend in the variation in the parameter, that is to say the evolution of the continuous curve in the immediate future, can be read out more or less "manually" from the continuous curve displayed on the viewing screen only if the time axis is chosen as suitably small. Basically, however, the time axis of the continuous curve can be chosen as desired and, in particular, independently of the current values, with the result that it is not always possible to detect the trend reliably from the continuous curve displayed. For the numerical processing of the continuous curve, the time axis may more or less be chosen as small as desired, with the result that the expected evolution of the continuous curve can be detected appreciably earlier with the aid of the trend arrow.

Various possibilities exist for the positioning of the trend arrow within the datum-line display. An embodiment is preferred in which the trend arrow is disposed adjacently to the more recent end of the continuous curve on the viewing screen. It is likewise possible to dispose the deviation bar between the trend arrow and the more recent end of the continuous curve.

Of interest is an embodiment in which the orientation of the trend arrow depends on the particular value of the instantaneous slope. For example, the trend arrow points upward for a positive instantaneous slope and downward for a negative instantaneous slope. At the same time, the trend arrow may point upward or downward to a different extent depending on the magnitude of the instantaneous slope and, in particular, may be vertically aligned.

It may furthermore also be expedient to design the trend arrow as a flashing signal in the case of extreme values of the instantaneous slope, in which case the flashing frequency may again depend here on the value of the instantaneous slope.

It is clear that, for one embodiment, the display of the continuous curve may also be deactivated, with the result that it is not imaged for certain applications of the datum-line display.

In a particularly advantageous embodiment, a respective separate datum-line display may be generated for a plurality of different parameters in such a way that a plurality of datum-line displays are disposed horizontally next to one another on the viewing screen and that the baselines of horizontally adjacent datum-line displays are coaxially in alignment with one another on the viewing screen. This embodiment utilizes the insight that the user concerned can detect deviations from a reference state, represented by the baselines in the case of a plurality of parameters more or less at a glance if the baselines all lie on a common horizontal line since, in this display, the baselines that are in alignment with one another create a common datum line for all the parameters. Deviations upward or downward from said common datum line can be perceived particularly easily by the user on the basis of experience. The user consequently sees immediately whether one of the deviation bars is unusually far away from the datum line upward or downward. This appreciably simplifies the simultaneous monitoring of a plurality of selected parameters. The user can draw conclusions about specific situations and evolutions of the system from the pattern of deviation bars and trend arrows. In other words, the datum-line display according to the invention consequently makes possible a pattern recognition.

Further important features and advantages of the invention emerge from the subclaims, from the drawings and from the associated Figure descriptions by reference to the drawings.

It goes without saying that the abovementioned features and those still to be explained below can be used not only in the combination specified in each case, but also in other combinations or on their own without departing from the scope of the present invention.

These and other aspects of the invention are apparent from and will be elucidated with reference to a preferred exemplary embodiment described hereinafter and shown in the drawings, in which identical reference symbols relate to identical or functionally identical or similar components.

Figure 2:
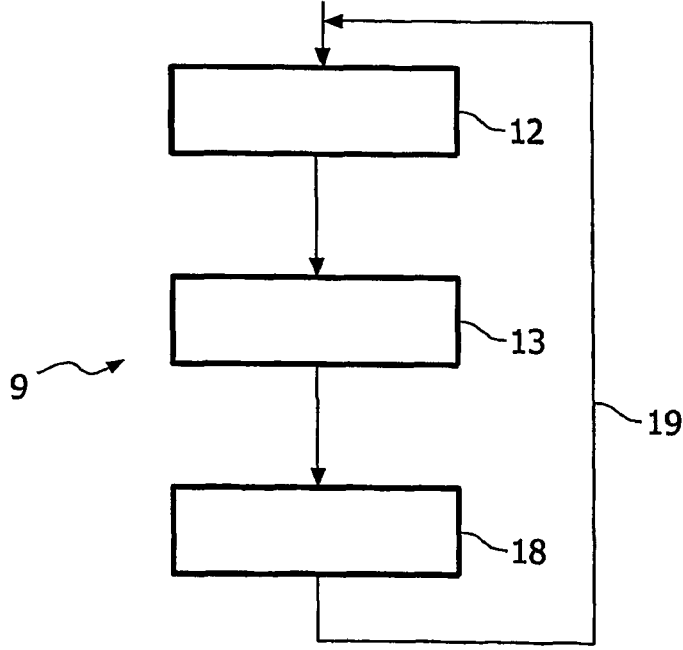
Figure 3:
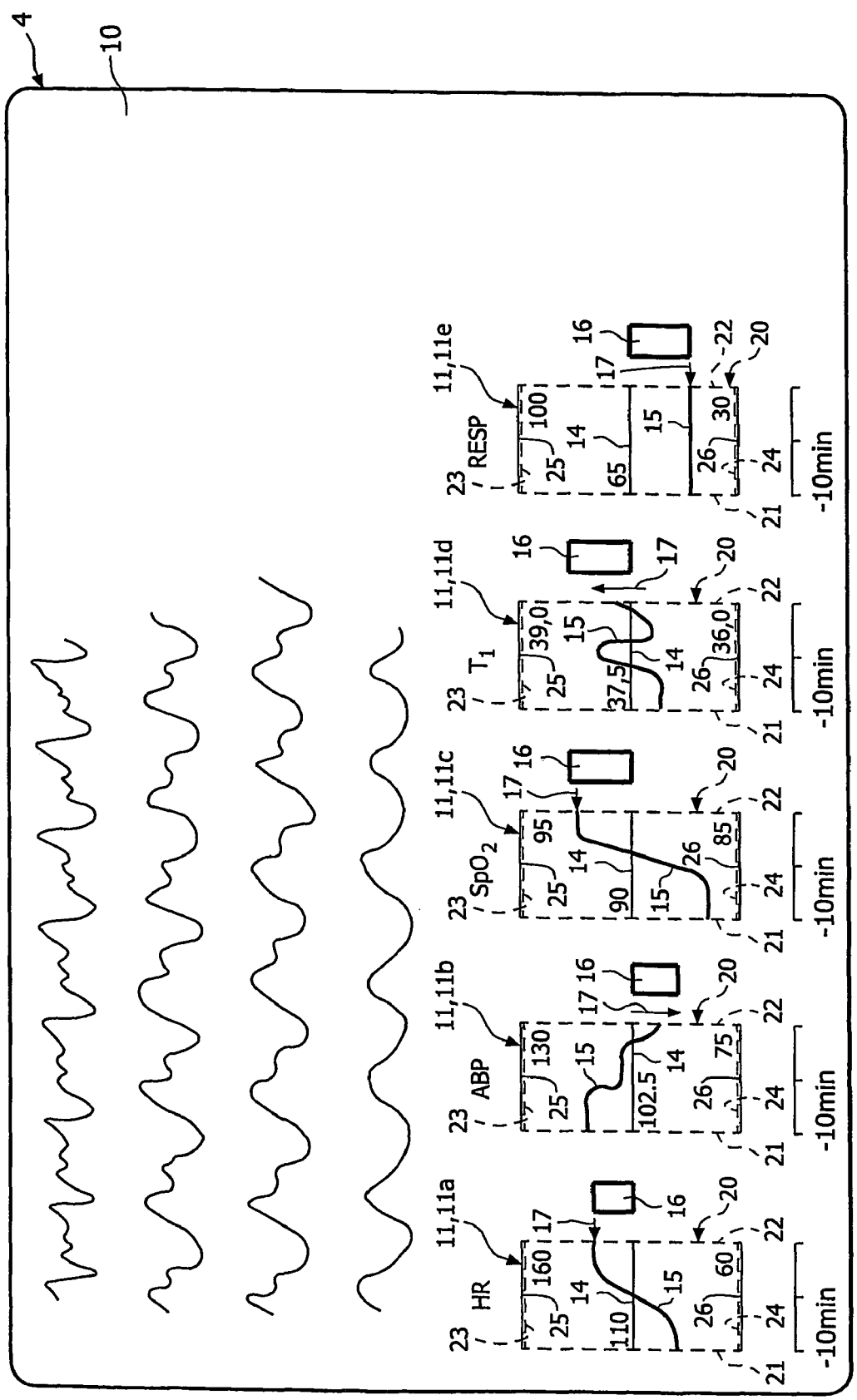

In the drawings:

FIG. 1 shows diagrammatically a basic circuit diagram of a device according to the invention, FIG. 2 shows diagrammatically a simplified flowchart explaining the method according to the invention, FIG. 3 shows diagrammatically a simplified view of a viewing screen on which a plurality of datum-line displays according to the invention are displayed.

According to FIG. 1, a device 1 according to the invention comprises a computer or calculator 2, a user interface 3 and a viewing screen 4 that are interconnected via suitable data lines and/or signal lines 5. It is clear that the calculator or computer 2 may also be a computer system comprising a plurality of computers or calculators. For example, at least a first calculator may serve to log parameters, while at least a second calculator may process the logged parameters and, for example, display them on a viewing screen. What is explained below for the computer or calculator 2 applies correspondingly also to a computer system or a calculator system.

Connected to the computer 2 is a plurality of sensors 6, in this case four, via suitable lines 7. It is clear that, depending on the particular application case, also more or less than four sensors 6 may be connected to the computer 2. The computer 2 is constructed in such a way that a computer program 8 can run in it. The user interface 3 may comprise, for example, a keyboard and/or a computer mouse and/or a touch screen, the viewing screen 4 then expediently having the touchscreen function.

Using the sensors 6, the device interacts with a system not shown here and as a rule logs a multiplicity of parameters that characterize the current state of the system. The device therefore serves to monitor said system, which takes place by observing and analyzing said parameters.

Without limiting the generality, the system to be monitored is preferably a patient whose body functions have to be monitored in order to be able to react promptly and appropriately if critical states, undesirable embodiments or deviations from an initial state occur. For example, the body functions of a patient are continuously monitored in an intensive care unit, in an accident admission department or in an operating theater. The individual physical parameters that characterize the body functions of the patient are, for example, blood pressure, respiratory rate, oxygen saturation, pulse, ventilation, etc. Normally, a multiplicity of parameters is monitored and displayed on the viewing screen 4. In that case, numerical displays and also graphical displays of continuous curves and real-time curves are normal. In order to be able to extract the data relevant for the patient concerned from the multiplicity of information items displayed on the viewing screen 4, increased attention is required of the user, that is to say typically of doctors and nursing staff. It is clear that the device 1 processes the data logged by means of the sensors 6 more or less in real time and displays them on the viewing screen 4.

In order to make the current state of the system, that is to say of the patient, more easily detectable, the device 1 is designed in such a way that it can perform a method according to the invention that is explained in greater detail by reference to FIG. 2. In this connection, it is clear that the computer program 8 is advantageously designed in such a way that it is suitable for activating the device 1 for the purpose of performing the method according to the invention provided that the computer program 8 is running in the computer 2 of the device 1.

FIG. 2 shows a detail 9 of a flowchart that reflects the course of the method according to the invention when a datum-line display is displayed on the viewing screen 4 for the purpose of monitoring the system concerned for at least one parameter of the system.

In FIG. 3, a plurality of such datum-line displays, for example five, are displayed on a viewing screen 10 shown by way of example, each being denoted by 11 or 11a to 11e. In this case, every datum-line display 11 is assigned to another system parameter. For example, the first datum-line display 11a shown on the left serves to visualize the heart rate. The second datum-line display 11b disposed alongside is assigned to the arterial blood pressure. The third datum-line display 11c represents the oxygen saturation. The fourth datum-line display 11d represents a body temperature and the fifth datum-line display 11e reflects the respiratory rate. It is clear that said parameters are only exemplary, so that, in particular, other parameters can also be displayed on the viewing screen 4 by means of such a datum-line display 11. An embodiment is even preferred in which the user concerned can select a small number of desired parameters from the multiplicity of monitored parameters in order to display them in each case by means of the datum line display 11 on the viewing screen 4. The parameter concerned is expediently selected individually for the patient concerned. Expediently, those parameters are selected that are the most meaningful for assessing the current state.

Returning to FIG. 2, a variation with time of the values of the parameter concerned is logged in a step 12 for every parameter that is to be displayed with the aid of a datum-line display 11 on the viewing screen 4. In this connection, it is clear that the physiological parameters are logged in the normal way, so that, for example, the current heart rate is determined from a plurality of consecutive heart beats. In step 12, a base value is simultaneously determined for the parameter concerned, which value is used in the subsequent steps 13 and 18. The way in which the base value can be determined is dealt with in greater detail below. In addition, an instantaneous deviation between the above mentioned base value and the current parameter value in each case is determined in step 12. Alternatively, instead of the current parameter value, a current mean value may also be used that is determined from a specified group of consecutive parameter values, said parameter-value group containing the current parameter value. In this way, so-called outliers can be compensated for. At the same time, it may be expedient in taking mean values to weight the individual values of the parameter-value group differently, and in particular it appears expedient to weight the current parameter value more heavily than the preceding parameter values.

The base value of the parameter concerned is chosen in such a way that it represents a parameter value in which a stable patient status exists. The base value does not therefore necessarily have to be a parameter value that exists in the case of a healthy patient. It is likewise possible to select for the base value a target value that the parameter concerned is to reach in the case of a correct treatment process. The base value may be specified by the user concerned. For example, the user may select the base value individually for the patient concerned. It is likewise possible that the base value is determined automatically.

In addition to the base value, the user may also set an upper limit value and a lower limit value for permissible values of the parameter concerned. Here, again, the setting is expediently matched individually to the patient concerned. If the base value is automatically specified, the numerical mean value, for example, can be used between the upper limit value and the lower limit value for the base value.

According to the embodiment shown here, the trend, that is to say the instantaneous slope in the value variation with time, can, in addition, be determined for the current parameter value in step 12.

In a subsequent step 13, a baseline 14 (cf. FIG. 3) is now created that represents the base value determined in the preceding step 12 and is shown in FIG. 3. In step 13, a continuous curve 15 (cf. FIG. 3) is created that represents the variation with time of the parameter values for a predetermined time interval. The time interval for which the respective continuous curve 15 is to be created can be set by the user. In addition, said continuous curve 15 is normalized with respect to the baseline 14, i.e. the baseline 14 and the continuous curve 15 are based on the same coordinate system. Consequently, the continuous curve 15 has the base value at an intercept with the baseline 14.

In addition, in step 13, a deviation bar 16 (cf. FIG. 13) is created for each parameter of the datum-line displays 11. In this connection, said deviation bar 16 represents the instantaneous deviation determined in step 12 and is likewise normalized with respect to the baseline 14. The normalization of the deviation bar 16 with respect to the baseline 14 has the result that the deviation bar 16 has the same ordinate value with respect to the baseline 14 for the current parameter value concerned, which ordinate value said parameter value also has in the continuous curve 15 as soon as it is imaged therein.

In the preferred variant shown here, a trend arrow 17 (cf. FIG. 3) that represents the associated instantaneous slope determined in step 12 at least in regard to its sign is created, in addition, in step 13 for each of the parameters of the datum-line displays 11.

In accordance with FIG. 2, the step 13 is followed by a step 18 in which the component created in the preceding step 13 of the respective datum-line display 11 is now displayed on the viewing screen 4. In detail, the baseline 14, the continuous curve 15, the deviation bar 16 and here additionally the trend arrow 17 are consequently displayed on the viewing screen 4 for every datum-line display 11. In this connection, the baseline 14 is displayed in each case on the viewing screen 4 in such a way that it extends horizontally on the viewing screen 4 and with a specified length measured in the horizontal direction. The length of the baseline 14 may at the same time be set by the user.

For the case where, as here, a plurality of datum-line displays 11 are simultaneously displayed on the same viewing screen 4, the display preferably takes place in such a way that the datum-line displays 11 are disposed horizontally next to one another on the viewing screen 4. Of particular interest in this connection is the variant shown here, in which the baselines 14 of the horizontally adjacent datum-line displays 11 are in alignment and form a common datum line for all the datum-line displays 11 disposed next to one another. The arrangement of the datum-line displays 11 or the alignment of the baselines 14 is of particular importance for the rapid recognizability of the information items displayed in the individual datum-line displays 11.

The continuous curves 15 on the viewing screen 4 are displayed, according to the invention, in such a way that, on the one hand, the time axes of the continuous curves 15 each extend horizontally on the viewing screen 4 and that, on the other hand, the continuous curves 15 each extend essentially over the entire length of the associated baseline 14. However, the baseline 14 at the same time represents the time axis of the associated continuous curve 15 in its direction of extension. The numerical value of this time axis, that is to say the magnitude of the time interval displayed by the continuous curve 15, can be selected by the user without the geometrical length of the baseline 14, which can be set separately by the user, varying in the process. A suitable time period, for example 15 or 30 minutes, is expedient for the selection of the time window displayed by the continuous curve 15.

Within every datum-line display 11, the associated deviation bar 16 is displayed on the viewing screen 4 in such a way that it extends in the vertical direction from the level of the associated baseline 14. Preferred in this connection is an embodiment in which the more recent end of the continuous curve 15 is situated at the right-hand side of the datum-line display 11, with the result that the continuous curve 15 represents increasingly older parameter values to the left. In operating the device 1, the measured values are constantly updated so that the continuous curve 15 gradually passes from right to left through the time window concerned.

The normalization of the deviation bar 16 with respect to the baseline 14 has, inter alia, the consequence that the deviation bar 16 projects upward from the baseline 14 for current parameter values that are greater than the base value, whereas it projects downward from the baseline 14 if the current parameter value is less than the base value 14.

Furthermore, in the preferred embodiment shown here, the trend arrow 17 is displayed on the viewing screen 4 in step 18, and specifically, for example, in such a way that, like the deviation bar 16, the trend arrow 17 is disposed on the viewing screen 4 adjacently to the more recent end of the associated continuous curve 15. Expediently, the trend arrow 17 is positioned under these circumstances between the more recent end of the continuous curve 15 and the associated deviation bar 16 on the viewing screen 4. The deviation bar 16 can likewise be disposed between the more recent end of the continuous curve 15 and the trend arrow 17. In principle, however, any desired positionings are possible for the trend arrow 17 and/or for the deviation bar 16. In an arrangement in which continuous curve 15, deviation bar 16 and trend arrow 17 follow one another from left to right, this corresponds essentially to the time sequence of past, present and future, which improves an intuitive information transfer of the datum-line display 11. For the case where the instantaneous slope is positive as in the fourth datum-line display 11*d*, a trend arrow 17 is generated that points to a greater or lesser extent upward, in particular vertically. If, however, the instantaneous slope is negative as, for example, in the second datum-line display 11*b*, the trend arrow 17 points to a greater or lesser extent downward, in particular vertically. A trend arrow 17 pointing upward or downward, respectively, consequently indicates that the parameter concerned increases or decreases in a relatively short time window comprising the current point in time, from which the observer concerned can detect, at least for the immediate future, in which direction the parameter concerned is evolving.

The orientation of the trend arrow 17 may depend in this connection on the magnitude of the instantaneous slope, with the result that the trend arrow 17 points, in the case of fairly large instantaneous slopes, more steeply upward or downward and, in the case of fairly small instantaneous slopes, points upward or downward at a comparatively small angle. In addition or alternatively, the trend arrow 17 may be displayed in the case of specified limit values of the instantaneous slope as a flashing signal whose flashing frequency may additionally depend on the value of the instantaneous slope.

For the case where the parameter concerned has remained essentially constant in the time window relevant for the determination of the instantaneous slope, the trend arrow 17 is displayed in step 18 in such a way that it points in the vertical direction at the more recent end of the associated continuous curve 15. The instantaneous slope therefore has approximately the value zero and is at least in a specified interval containing the value zero. In the example shown in FIG. 3, the parameters of the first, third and fifth datum-line displays 11*a*, 11*c* and 11*e* are constant in the relevant time period, with the result that the instantaneous slope has in each case the value zero in the current parameter value. Accordingly, in said datum-line displays 11*a*, 11*c*, 11*e*, each of the trend arrows 17 points horizontally to the left at the right-hand, that is to say more recent, end of the associated continuous curve 15.

The loop 19 shown in FIG. 2 indicates that the datum-line displays 11 are constantly updated while the device 1 is in operation and the method according to the invention is running.

According to FIG. 3, each datum-line display 11 is assigned a rectangular window 20 symbolized by a broken line that is normally not displayed on the viewing screen 4. The rectangular window 20 has a left-hand side 21 and a right-hand side 22 that extend parallel to one another and perpendicularly to the baseline 14. Furthermore, the rectangular window 20 has an upper side or top side 23 and a lower side or bottom side 24 that each extend parallel to the baseline 14. The rectangular window 20 is, for example, disposed here with respect to the baseline 14 and dimensioned in such a way that the baseline 14 is disposed in the geometric center between the top side 23 and the bottom side 24 and, in addition, extends from the left-hand side 21 to the right-hand side 22. The baseline 14 may also likewise be disposed at any other desired position between the top side 23 and the bottom side 24. Furthermore, the baseline 14 does not necessarily have to extend completely up to the left-hand side 21 and/or up to the right-hand side 22. Assigned to the top side 23 is the specified upper limit value of the parameter concerned. In a corresponding way, the lower limit value specified for the parameter concerned is also assigned to the bottom side 24. Of particular importance in this connection is that both the continuous curve 15 and the deviation bar 16 of the datum-line display 11 are normalized with respect to the upper limit value and with respect to the lower limit value. This means that, when it intercepts the top side 23 or the bottom side 24, the continuous curve 15 has the upper limit value or the lower limit value, respectively, of the associated parameter at the intercept. In a corresponding way, the current parameter value corresponds to the upper limit value if the deviation bar 16 extends up to the level of the top side 23; or the current parameter value corresponds to the lower limit value if the deviation bar 16 extends down to the level of the bottom side 24.

According to the embodiment shown here, an upper limit-value line 25 and a lower limit-value line 26 can in each case be generated for the datum-line displays 11 in steps 13 and 18 and displayed on the viewing screen 4. In this connection, the upper limit-value line 25 represents the upper limit value and extends on the top side 23 of the rectangular window 20 essentially over the entire length of the baseline 14. Accordingly, the upper limit-value line 25 is essentially congruent with the top side 23. In the same way, the lower limit-value line 26 represents the lower limit value and extends congruently over the bottom side 24 of the rectangular window 20. Accordingly, the lower limit-value line 26 also extends essentially over the entire length of the baseline 14. The limit values in relation to the baseline 14 are particularly clearly visualized with the aid of the limit-value lines 25, 26. In addition, the relative position of the continuous curve 15 and of the deviation bar 16 within the limit values and relative to the base value can be recognized at a glance.

In addition, it is of particular importance that the geometrical shape of the rectangular window 20 is specified or can be specified independently of the limit values of the parameter concerned. In other words, the geometrical spacings between the upper limit-value line 25 and the baseline 14, on the one hand, and the lower limit-value line 26 and the baseline 14, on the other hand, are always equal in size, while the numerical spacings between upper limit value and base value, on the one hand, and lower limit value and base value, on the other hand, may be different. In this way, the relation of a deviation of the continuous curve 15 and of the deviation bar 16 from the baseline 14 can be comprehended intuitively and directly with regard to the nearer limit-value line 25 or 26 in each case.

Furthermore, the horizontal extension of the rectangular window 20 is expediently chosen as equal in size for all the horizontally adjacent datum-line displays 11 in order also to avoid confusing the observer here. Expediently, the time windows assigned to the continuous curves 15 are also chosen as of equal size for all the datum-line displays 11 displayed simultaneously in order thereby to simplify the recognition of correlations between individual parameters.

If, as in the preferred exemplary embodiment shown here, a plurality of datum-line displays 11 are simultaneously displayed horizontally next to one another on the viewing screen 4, it is advantageous to dimension the rectangular window 20 of the adjacent datum-line displays 11 in such a way that, on the one hand, their top sides 23 are coaxially in alignment with one another and, on the other hand, their bottom sides 24 are also coaxially in alignment with one another. In connection with the upper limit-value lines 25 and lower limit-value lines 26 displayed on the viewing screen 4, a common upper limit-value line and a common lower-limit line are consequently produced visually for the observer. This mode of display normalizes the individual datum-line displays 11 so that the observer can immediately detect, from the relative position of the continuous curves 15 and the deviation bars 16 within the associated limit-value lines 25, 26 and with respect to the associated baseline 14, which parameter deviates noticeably from the stable state (represented by the baseline 14) and/or approaches in a critical way one of the limit values (represented by the respective limit-value line 25, 26) or is situated in its vicinity. Noticeable in this connection is the fact that the user concerned can extract the essential information items from the datum-line displays 11 at a glance without it being necessary to read off any numerical values or to take account of alphanumerical indicators. Consequently, the user can more or less intuitively acquire the desired information items with the aid of the datum-line displays 11 according to the invention very much more rapidly and use them for a decision. In particular, it is possible in stress situations to reduce the danger of a reading error and the danger of an incorrect decision.

To create the datum-line displays 11, it may be expedient not to take account in each case of the current parameter value in the continuous curve 15 since this is in any case visualized in the deviation bar 16. The continuous curve 15 then logs in the specified time period only the parameter values preceding the current parameter value. This variant is particularly clearly recognizable in the second and in the fourth datum-line displays 11$b$, 11$d$ since, in those cases, the ordinate segment of the deviation bar 16 concerned has a value other than the more recent end of the continuous curve 15 concerned.

In order to separate the individual datum-line displays 11 better visually from one another, it may be advantageous in an embodiment of the device 1 according to the invention or of the method according to the invention to display, within the datum-line display 11 concerned, the continuous curve 15, the deviation bar 16 and, if present, the limit-value lines 25, 26 on the viewing screen 4 using the same color, while different colors are assigned to the individual, separate datum-line displays 11. In order to reinforce the nature of the common datum line, the baseline 14 may, however, be displayed uniformly using the same color for all the adjacent datum-line displays 11.

The datum-line displays 11 proposed according to the invention, which can, in principle, be generated for any desired parameter of the system to be monitored, preferably a patient, make it possible for the monitoring staff to detect variations in the state of the system for the selected parameters visualized by means of the datum-line displays 11 more or less at a glance.

A linear relationship may be provided between the numerical deviation of the parameter values from the base value and the geometrical deviation actually shown on the viewing screen 4 of the parameter values in the continuous curve 15 or in the deviation bar 16 with respect to the baseline 14. An exponential relationship may likewise be specified, in which case, for example, smaller numerical deviations cause only relatively small geometrical deviations, while greater numerical deviations result in disproportionately greater geometrical deviations. In this way, deviations in the actual state (represented by the continuous curve 15 and deviation bar 16) from the desired state (represented by the baseline 14) are emphasized more strongly if they deviate to a greater extent from the baseline 14, as a result of which the observer's attention is focused on the greater deviations. This improves the early detection of a critical parameter.

As a result of the high detection value of the datum-line displays 11, the monitoring staff can carefully take a decision for the further treatment of the patient, which can increase the probability of recovery or of a stabilization of the patient's state.

LIST OF REFERENCE SYMBOLS

1 Device
2 Computer
3 User interface
4 Viewing screen
5 Data and/or signal line
6 Sensor
7 Line
8 Computer program
9 Flowchart
10 Viewing screen picture
11 Datum-line display
12 First step in 9
13 Second step in 9
14 Baseline
15 Continuous curve
16 Deviation bar
17 Trend arrow
18 Third step in 9
19 Loop in 9
20 Rectangular window
21 Left-hand side of 20
22 Right-hand side of 20
23 Top side of 20
24 Bottom side of 20
25 Upper limit-value line
26 Lower limit-value line

The invention claimed is:

1. A method for monitoring a system in which a datum-line display is generated on a viewing screen for at least one parameter of the system as follows:
logging of a variation with time of the values of the parameter concerned,
determination of a base value for the parameter concerned,
determination of an instantaneous deviation between the base value and the current parameter value or a current mean value of a specified group, containing the current parameter value, of consecutive parameter values,
creation of a baseline representing the base value,
display of the baseline on the viewing screen in such a way that the baseline extends horizontally on the viewing screen and with a specified length,
creation of a continuous curve that represents the variation with time of the parameter values for a specified time period and is normalized with respect to the baseline,
display of the continuous curve on the viewing screen in such a way that the continuous curve's time axis extends horizontally on the viewing screen and that the continuous curve on the viewing screen essentially extends over the entire length of the baseline,
creation of a deviation bar that represents the instantaneous deviation and is normalized with respect to the baseline,
display of the deviation bar on the viewing screen in such a way that the deviation bar extends vertically on the viewing screen from the level of the baseline, wherein the datum-line display has a trend arrow that is generated as follows:
determination of the trend of the value variation with time in the current parameter value,
creation of the trend arrow, which represents the trend,
display of the trend arrow on the viewing screen and wherein the trend arrow is displayed on the viewing screen in such a way that the trend arrow points upward in the case of a positive instantaneous slope and points downward in the case of a negative instantaneous slope.

2. A method as claimed in claim 1, wherein the trend arrow is displayed on the viewing screen in such a way that the trend arrow is disposed adjacently to one end of the continuous curve on the viewing screen.

3. A method as claimed in claim 1, wherein the trend arrow is disposed between the continuous curve and the deviation bar on the viewing screen, or in that the trend arrow is disposed on the viewing screen in such a way that the deviation bar is situated between the trend arrow and the continuous curve.

4. A method for monitoring a system in which a datum-line display is generated on a viewing screen for at least one parameter of the system as follows:
logging of a variation with time of the values of the parameter concerned,
determination of a base value for the parameter concerned,
determination of an instantaneous deviation between the base value and the current parameter value or a current mean value of a specified group, containing the current parameter value, of consecutive parameter values,
creation of a baseline representing the base value,
display of the baseline on the viewing screen in such a way that the baseline extends horizontally on the viewing screen and with a specified length,
creation of a continuous curve that represents the variation with time of the parameter values for a specified time period and is normalized with respect to the baseline,
display of the continuous curve on the viewing screen in such a way that the continuous curve's time axis extends horizontally on the viewing screen and that the continuous curve on the viewing screen essentially extends over the entire length of the baseline,
creation of a deviation bar that represents the instantaneous deviation and is normalized with respect to the baseline,
display of the deviation bar on the viewing screen in such a way that the deviation bar extends vertically on the viewing screen from the level of the baseline, wherein the datum-line display has a trend arrow that is generated as follows:

determination of the trend of the value variation with time in the current parameter value, creation of the trend arrow, which represents the trend, display of the trend arrow on the viewing screen and wherein the orientation of the trend arrow depends on the value of the instantaneous slope.

5. A method for monitoring a system in which a datum-line display is generated on a viewing screen for at least one parameter of the system as follows:

logging of a variation with time of the values of the parameter concerned, determination of a base value for the parameter concerned, determination of an instantaneous deviation between the base value and the current parameter value or a current mean value of a specified group, containing the current parameter value, of consecutive parameter values, creation of a baseline representing the base value, display of the baseline on the viewing screen in such a way that the baseline extends horizontally on the viewing screen and with a specified length, creation of a continuous curve that represents the variation with time of the parameter values for a specified time period and is normalized with respect to the baseline, display of the continuous curve on the viewing screen in such a way that the continuous curve's time axis extends horizontally on the viewing screen and that the continuous curve on the viewing screen essentially extends over the entire length of the baseline, creation of a deviation bar that represents the instantaneous deviation and is normalized with respect to the baseline, display of the deviation bar on the viewing screen in such a way that the deviation bar extends vertically on the viewing screen from the level of the baseline, wherein the datum-line display has a trend arrow that is generated as follows:

determination of the trend of the value variation with time in the current parameter value, creation of the trend arrow, which represents the trend, display of the trend arrow on the viewing screen and wherein the trend arrow points in the vertical direction at one end of the continuous curve if the instantaneous slope has the value zero or is in a specified interval containing the value zero.

6. A method for monitoring a system in which a datum-line display is generated on a viewing screen for at least one parameter of the system as follows:

logging of a variation with time of the values of the parameter concerned, determination of a base value for the parameter concerned, determination of an instantaneous deviation between the base value and the current parameter value or a current mean value of a specified group, containing the current parameter value, of consecutive parameter values, creation of a baseline representing the base value, display of the baseline on the viewing screen in such a way that the baseline extends horizontally on the viewing screen and with a specified length, creation of a continuous curve that represents the variation with time of the parameter values for a specified time period and is normalized with respect to the baseline, display of the continuous curve on the viewing screen in such a way that the continuous curve's time axis extends horizontally on the viewing screen and that the continuous curve on the viewing screen essentially extends over the entire length of the baseline, creation of a deviation bar that represents the instantaneous deviation and is normalized with respect to the baseline, display of the deviation bar on the viewing screen in such a way that the deviation bar extends vertically on the viewing screen from the level of the baseline and wherein the display of the continuous curve can be deactivated.

7. A method as claimed in claim 6, wherein the datum-line display has a rectangular window whose top side and bottom side extend parallel to the baseline and have the same geometrical spacing in the vertical direction from the baseline, wherein a specified upper limit value for the parameter concerned is assigned to the top side, wherein a specified lower limit value for the parameter concerned is assigned to the bottom side, wherein the continuous curve and the deviation bar are, in addition, normalized with respect to the upper limit value and the lower limit value.

8. A method as claimed in claim 7, wherein an upper limit-value line representing the upper limit value is created and is displayed on the viewing screen in such a way that it essentially extends over the entire length of the baseline on the top side of the rectangular window, wherein a lower limit-value line representing the lower limit value is created and is displayed on the viewing screen in such a way that it essentially extends over the entire length of the baseline on the bottom side of the rectangular window.

9. A method as claimed in claim 7, wherein the limit values have different numerical spacings from the base value although the top side and the bottom side have the same geometrical spacing from the baseline on the viewing screen.

10. A method as claimed in claim 7, wherein the top sides of the rectangular windows of horizontally adjacent datum-line displays are disposed coaxially in alignment with one another on the viewing screen, wherein the bottom sides of the rectangular windows of horizontally adjacent datum-line displays are disposed coaxially in alignment with one another on the viewing screen.

11. A method as claimed in claim 6, wherein the continuous curve does not cover the current parameter value, but those parameter values that precede the current parameter value in a specified time period.

12. A method as claimed in claim 6, wherein a separate datum-line display is generated in each case for a plurality of different parameters in such a way that a plurality of datum-line displays are disposed horizontally next to one another on the viewing screen and in that the baselines of horizontally adjacent datum-line displays are disposed coaxially in alignment with one another on the viewing screen.

13. A method as claimed in claim 6, wherein at least one parameter can be selected from a plurality of different parameters of the system for which parameter or parameters a datum-line display is generated in each case.

14. A method as claimed in claim 6, wherein the system to be monitored is a patient.

15. A method for monitoring a system in which a datum-line display is generated on a viewing screen for at least one parameter of the system as follows:

logging of a variation with time of the values of the parameter concerned, determination of a base value for the parameter concerned, determination of an instantaneous deviation between the base value and the current parameter value or a current mean value of a specified group, containing the current parameter value, of consecutive parameter values, creation of a baseline representing the base value, display of the baseline on the viewing screen in such a way that the baseline extends horizontally on the viewing screen and with a specified length, creation of a continuous curve that represents the variation with time of the parameter values for a specified time period and is normalized with respect to the baseline, display of the continuous curve on the viewing screen in such a way that the continuous curve's time axis extends horizontally on the viewing screen and that the continuous curve on the viewing screen essentially extends over the entire length of the baseline, creation of a deviation bar that represents the instantaneous deviation and is normalized with respect to the baseline, display of the deviation bar on the viewing screen in such a way that the deviation bar extends vertically on the viewing screen from the level of the baseline and wherein the deviation bar extends on the viewing screen adjacently to the more recent end of the continuous curve.

\* \* \* \* \*